United States Patent
Swaim

[19]

[11] Patent Number: 5,807,277
[45] Date of Patent: Sep. 15, 1998

[54] BIOPSY HAND TOOL FOR CAPTURING TISSUE SAMPLE

[76] Inventor: William R. Swaim, 2921 Sequoia Ct., Burnsville, Minn. 55337-3430

[21] Appl. No.: 573,333

[22] Filed: Dec. 15, 1995

[51] Int. Cl.$^6$ .................................................. A61B 10/00
[52] U.S. Cl. ........................... 600/567; 606/167; 606/170
[58] Field of Search .................................... 128/751–754, 128/757; 606/167, 170

[56] References Cited

U.S. PATENT DOCUMENTS

| | | |
|---|---|---|
| 1,867,624 | 7/1932 | Hoffman . |
| 2,198,319 | 4/1940 | Silverman . |
| 2,496,111 | 1/1950 | Turkel . |
| 2,516,492 | 7/1950 | Turkel . |
| 2,705,949 | 4/1955 | Silverman . |
| 2,919,692 | 1/1960 | Ackermann . |
| 3,175,554 | 3/1965 | Stewart . |
| 3,330,268 | 7/1967 | Goldsmith . |
| 3,477,423 | 11/1969 | Griffith . |
| 3,598,108 | 8/1971 | Jamshidi et al. . |
| 3,606,878 | 9/1971 | Kellog, Jr. . |
| 3,628,524 | 12/1971 | Jamshidi . |
| 3,683,892 | 8/1972 | Harris . |
| 3,850,158 | 11/1974 | Elias et al. . |
| 3,893,445 | 7/1975 | Hofsess . |
| 3,929,123 | 12/1975 | Jamshidi . |
| 3,989,033 | 11/1976 | Halpern et al. . |
| 4,543,966 | 10/1985 | Islam et al. ............................. 128/754 |
| 5,251,641 | 10/1993 | Xavier .................................... 128/754 |
| 5,257,632 | 11/1993 | Tuckel et al. ........................... 128/754 |
| 5,423,824 | 6/1995 | Akerfeldt et al. . |
| 5,429,138 | 7/1995 | Jamshidi . |

FOREIGN PATENT DOCUMENTS

| | | |
|---|---|---|
| 720843 | 2/1932 | France . |
| 142879 | 11/1953 | Sweden . |
| 171975 | 6/1965 | U.S.S.R. . |
| 249551 | 8/1969 | U.S.S.R. . |

OTHER PUBLICATIONS

Hyun et al., Fundamentals of Bone Marrow Examination, *Diagnostic Hematology*, Aug. 1994, pp. 651–662.
Page showing Westerman–Jensen technic for needle biopsy of bone and marrow, citing Arch. Int. Med., 114, 213, 1964.
Ahlstrom et al., CT–guided Bone Biopsy Performed by Means of a Coaxial Biopsy System with an Eccentric Drill, Radiology (journal), Aug. 1993, pp. 549–552, vol. 188.
Islam, A. et al., A New Bone Marrow Biopsy Needle With Core Securing Device, Technical Methods, 1981, pp.359–364, Great Britain.
Bone Marrow Biopsy—Aspiration Procedures: The Jamshidi Needle, 1971, five page instruction manual, U.S.A.

*Primary Examiner*—Max Hindenburg
*Assistant Examiner*—Pamela L. Wingood

[57] ABSTRACT

A biopsy device or hand tool for taking a sample of body tissue. The hand tool includes a stylus for forming an opening in relatively firm tissue such as the bone cortex, and a cannula formed by a pair of tubes for cutting and capturing a sample of a less firm tissue, such as bone marrow. The stylus is used initially when in the cannula and is withdrawn from the cannula after it has carved an opening in the bone cortex larger than the diameter of the outside diameter of the cannula. The cannula includes an outer elongate tube having a distal end portion with a cutting edge and opening and further includes an inner elongate tube having a distal end portion which also includes a cutting edge and opening. The tubes are rotatable relative to each other, an action which cuts off or at least partially cuts off the tissue connection which still exists to base tissue. Each of the distal end portions have tapering portions such that, when the tubes are rotated relative to each other, each of the tapering portions close off the opening of the other tube to thereby capture the body tissue sample to ensure removal of the sample from the body.

30 Claims, 5 Drawing Sheets

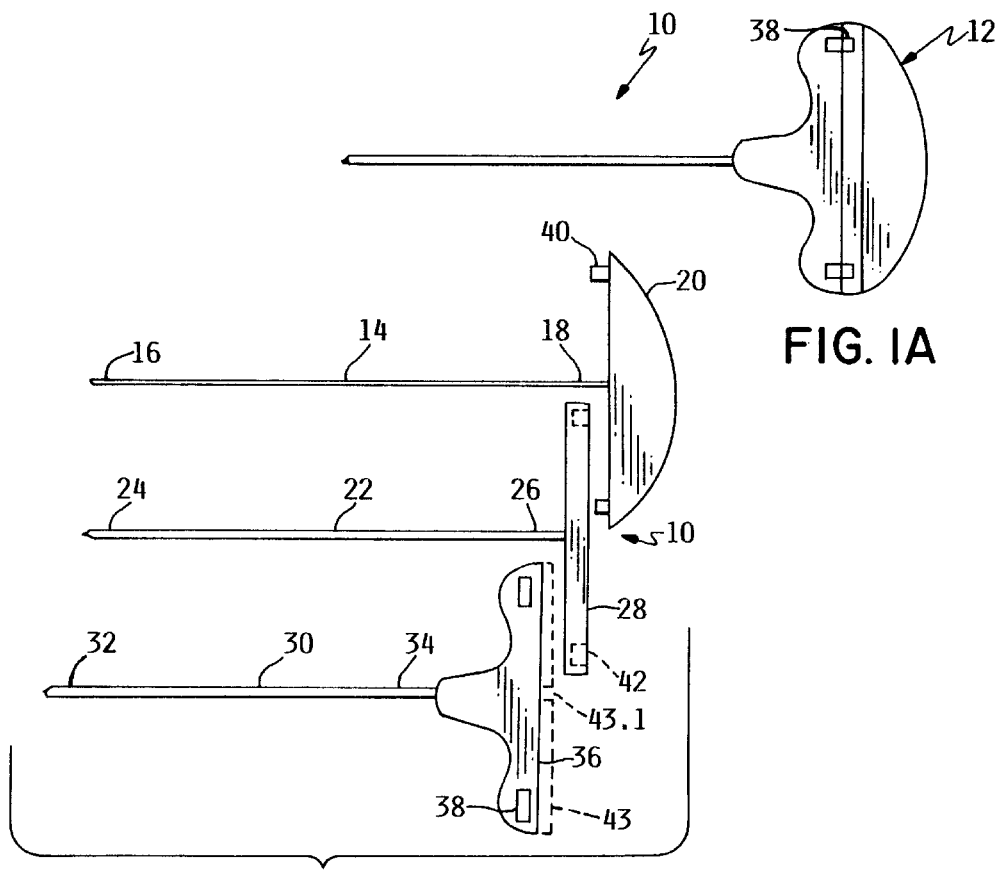
FIG. 1A
FIG. 1B
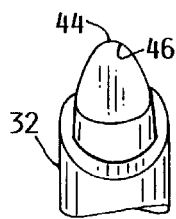
FIG. 2C
FIG. 2B
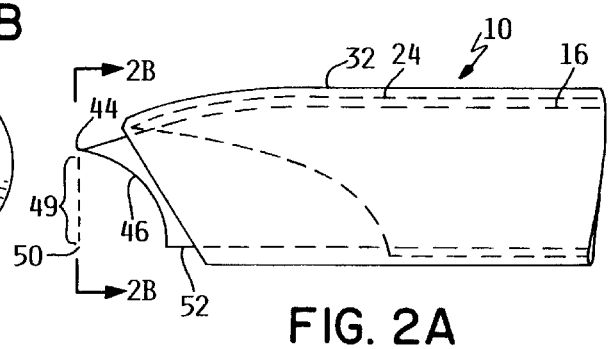
FIG. 2A
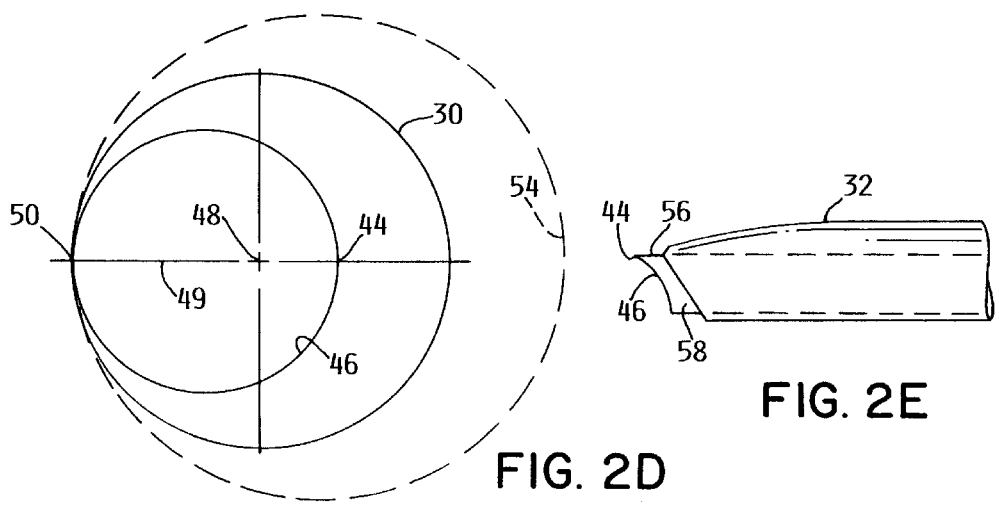
FIG. 2D
FIG. 2E

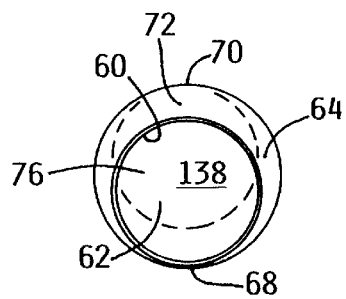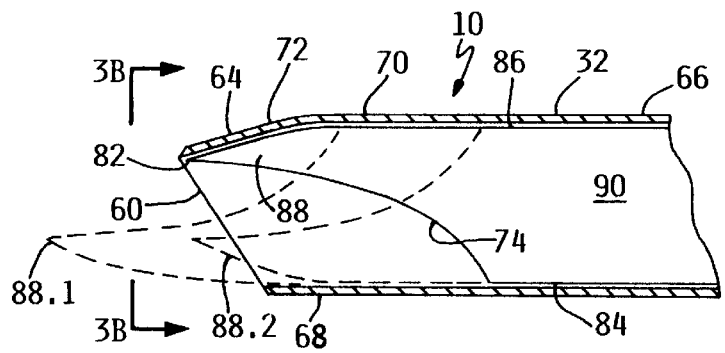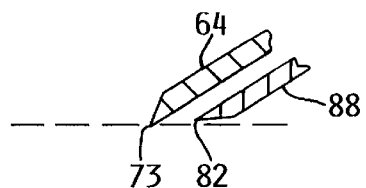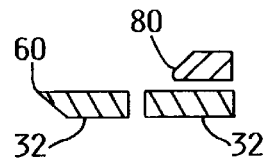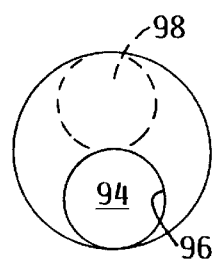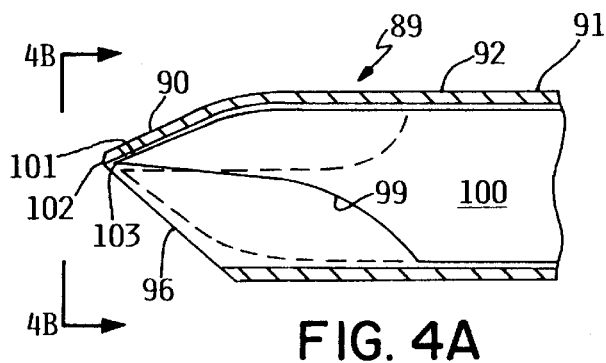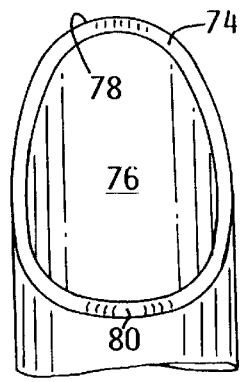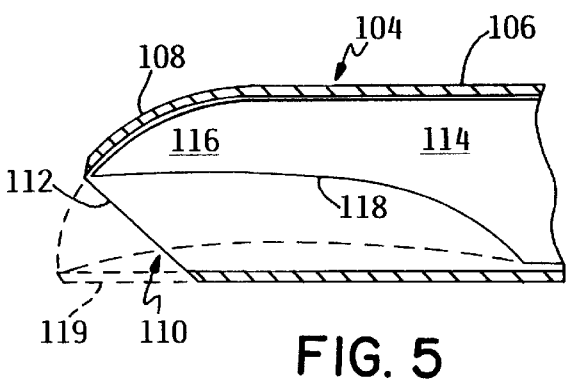

BIOPSY HAND TOOL FOR CAPTURING TISSUE SAMPLE

BACKGROUND OF THE INVENTION

The present invention relates generally to a medical device, particularly to a biopsy hand tool for obtaining a tissue sample, and specifically to such a hand tool for cutting and capturing a tissue sample without altering the architecture of the tissue sample and without permitting the tissue sample to slip out of the tool.

A biopsy device is an apparatus which takes a sample of body tissue. The biopsy device may be needle like and cut the sample from the body or draw the sample from the body by the creation of suction at the distal end of the needle like projection.

One type of biopsy device is a hand tool having a cannula and stylus. The stylus, located within the cannula and having a tip projecting from the cannula, is first utilized to carve a hole through tissue such as bone cortex. The stylus is then removed from the cannula, which remains in the body tissue and is inserted through the hole formed by the stylus and into tissue such as bone marrow. The cannula typically includes a tubular distal end with a cutting edge which penetrates into the bone marrow, a sample of which is thus received into the tube. The tube and sample are then removed from the body.

The architecture of the sample is important. Hence, biopsy devices having features for taking uncompressed samples having an unaltered architecture are essential for proper histologic interpretations.

One problem with prior art biopsy devices is that the hole formed in the body by the stylus has the same diameter, or a smaller diameter, as the cutting tube which is to be inserted through the hole. Accordingly, manipulation of the biopsy device or tool is limited. Manipulation of the cannula in the axial direction through the hole is difficult and may result in a wedging like action where the cannula is undesirably and dangerously forced through the hole. Further, manipulation such as tilting to cut off the connection between the sample and in vivo tissue (i.e., the tail of the sample or the uncut portion of the sample still connected to the in vivo tissue), may result in damage to or breakage of other tissue, such as the bone cortex, altering the architecture. This biopsy device solves these problems by creating an access through the bone cortex that has a diameter that is greater than the diameter of the cannula itself. This larger access hole permits a wider range of motion at all angles from the original axial direction. This permits greater access to a wider range of bone marrow tissue and allows multiple samples to be taken from a single site.

Another problem with prior art biopsy devices is that the sample, after being cut by the cutting tube, slips out of the biopsy device prior to the device being withdrawn from the body or prior to the sample being safely collected by the doctor. Such is especially a problem with very soft, or semi-liquid, loosely connected tissue as, for example, with multiple myeloma. Accordingly, the cannula must be reinserted and in some cases a new hole must be formed through the bone cortex with the stylus.

SUMMARY OF THE INVENTION

A general object of the present invention is to provide a unique tool and unique methods for taking a sample of body tissue.

Another object of the present invention is to provide a biopsy device with a unique stylus. Specifically, the stylus is provided with a tip off-center from the central axis of the cannula with a cutting edge that has an effective cutting length greater than one-half the diameter of the cannula such that the hole drilled by the stylus has a diameter greater than the cannula. Another unique feature of the stylus is a distal end with a scoop having relatively steep lateral cutting edges.

Another object of the present invention is to provide a biopsy device with a unique cannula. Specifically, the cannula includes outer and inner tubes, both of which include cutting edges at their distal ends and which are rotatable relative to each other such that the cutting edges make discrete and separate cuts in body tissue to more completely sever a sample of tissue from the body.

Another object of the present invention is to provide unique distal ends to the outer and inner tubes. Each of the distal ends includes an opening through which the tissue sample is received and a variably tapering portion which tapers outwardly from the opening toward the handle of the tool. Prior to rotation of the distal ends relative to each other, the openings and variably tapering portions are aligned with each other such that the tissue sample is readily received into the tool. After rotation of the distal ends relative to each other, the variably tapering portions confront each other and close off the others opening to effectively capture the tissue sample to prevent the sample from slipping out of the cannula.

Another object of the present invention is to provide a unique method of taking a sample of bone marrow with a stylus and cannula. The method includes forming with the stylus a hole in the bone cortex of a greater diameter than the diameter of the cannula used to take the sample.

Another object of the present invention is to provide a unique method of taking a sample of body tissue with a cannula having outer and inner tubes. The method includes moving the distal end portions relative to each other such that one of the distal end portions makes a cut in the body tissue sample in a direction at an angle to the axis of the cannula.

Another object of the present invention is to provide a unique range of motions for the cannula to permit cutting of the tissue connecting the in vivo tissue to the specimen. These motions include 180° rotation of the tubes relative to each other in a single plane, a 180° spiral rotation of the tubes relative to each other with an advance of the inner tube relative to the outer tube, and an advance of the inner tube relative to the outer tube without rotation.

An advantage of the present invention and its off-center stylus-created hole is that the cannula is permitted to readily enter the hole without being wedged into the hole and against the bone cortex. This provides easier access to the bone marrow. Further, less needles (stylus and cannula) are bent or broken.

Another advantage is that the relatively greater diameter of the off-center stylus created hole permits the cannula to in turn be of a relatively greater diameter relative to the size of the stylus to permit relatively large samples or multiple samples of tissue to be taken from a single site.

Another advantage is that the relatively great diameter of the hole in the bone cortex permits the cannula to be tilted to obtain additional samples from the same site and to make any requisites cuts of the connection between the cut specimen and in vivo tissue (the "tail" of the sample).

Another advantage of the present invention is that tissue is invaded only once because the present tool captures the sample. With the biopsy sample being captured by the variably tapered distal end portions confronting each other and closing off the opening through which the sample was taken, chances are lessened of further invasions at other tissue sites made necessary by a prior attempt or attempts to collect tissue samples which resulted in tissue samples slipping out of the cannula.

Another advantage is that less damage occurs to surrounding tissue during the single biopsy. Such an advantage is provided by the simple and minimal manipulation required by the hand tool. Rotation of the inner tube while holding the outer tube stationary minimizes harm to surrounding tissue. Further, since the connection between the specimen and the in vivo tissue is cut without tilting of the cannula, even less damage to surrounding tissue occurs.

Another advantage is that the architecture of the sample remains unaltered. The distal end of the inner tube includes a receiving portion of a greater diameter than the opening through which the specimen is initially received.

Another advantage is that multiple samples may be taken without withdrawing the cannula from the tissue (i.e. without withdrawing either the inner tube from the outer tube or the outer tube from the tissue). Accordingly, only one hole in the bone cortex is drilled by the stylus. Multiple samples may be taken by simply advancing the inner and outer tubes as a unit further into the tissue to gain access to another tissue site, or tilting the inner and outer tubes as a unit to gain access to another tissue site. Little chance exists that the previously taken samples will slide out of the inner tube when further samples are taken, even though the distal ends of the inner and outer tubes will move out of a confronting relationship, because in vivo tissue will block the escape of the previously taken samples and because the tubes distal ends are being moved a relatively short distance when gaining access to a new tissue site. With multiple samples, the probability of obtaining pathological samples is increased. Hence the chance for a better diagnosis is increased.

Another advantage is that the present biopsy hand tool is inexpensive to manufacture, and thus new and sterile tools may be used for each biopsy with used tools being disposed.

Another advantage is that the present biopsy hand tool is simple to use.

These and further objects and advantages of the present invention will become clearer in light of the following detailed description of the illustrative embodiments of this invention described in connection with the drawings.

BRIEF DESCRIPTION OF THE DRAWINGS

The illustrative embodiments may be best described by reference to the accompanying drawings where:

FIG. 1A shows an elevation view of the present biopsy hand tool.

FIG. 1B shows an exploded elevation view of the hand tool of FIG. 1A, including the stylus, the inner or capture tube, and the outer tube.

FIG. 2A shows a detail view of the distal ends of the stylus and outer tube and further shows in phantom the distal end of the inner tube.

FIG. 2B shows an end view of the stylus and outer tube of FIG. 2A.

FIG. 2C shows a view of the distal ends of the stylus and outer tube rotated along the axis of the cannula 90° from the view of FIG. 2A.

FIG. 2D shows a diagrammatic view of the hole created in the bone cortex by the stylus and the diameter of the hole relative to the diameter of the distal end of the outer tube and the cutting edge of the stylus.

FIG. 2E shows a detail, partially phantom view of an alternate embodiment of a stylus for the present invention wherein the stylus includes a generally cylindrical surface extending from its cutting tip to the handle of the tool.

FIG. 3A shows a detail view of the distal end of the cannula with the distal end of the outer tube shown in section and with the distal end of the inner tube shown before rotation relative to the outer tube (solid lines) and after such rotation (in phantom).

FIG. 3B shows an end view of the inner and outer tubes of FIG. 3A and also illustrates, via the lenticular portion, the connection between the specimen and the in vivo tissue which remains after rotation of the inner tube and its cutting edge.

FIG. 3C shows a view of the distal end of the inner tube rotated along the axis of the cannula 90° from the view of FIG. 3A.

FIG. 3D shows a detail view of the cutting edge of the outer tube relative to the cutting edge of the inner tube.

FIG. 3E shows a rounded portion of the distal edge of the inner tube which is noncutting.

FIG. 4A shows a detail view of the distal ends of an outer and inner tube cannula combination which provides for 100% capture of the biopsy sample.

FIG. 4B shows an end view of the distal ends of the outer and inner tube combination of FIG. 4A.

FIG. 5 shows a section, partially phantom view of an alternate cannula of the present invention which provides for a longitudinal sliding of the tubes relative to each other to cut off the connection between the specimen and the in vivo tissue.

Figure 6:
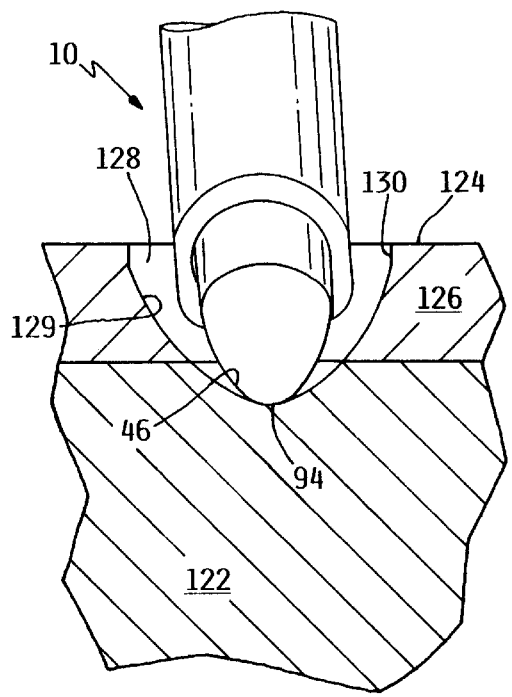
FIG. 6 shows a view of the stylus of the present invention penetrating bone cortex shown in section with bone marrow.

All Figures are drawn for ease of explanation of the basic teachings of the present invention only; the extensions of the Figures with respect to number, position, relationship, and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in the various figures of the drawings, the same numerals designate the same or similar parts. Furthermore, when the terms "inner", "outer", and "axial" and similar terms are used herein, it should be understood that these terms have reference only to the structure shown in the drawings as it would appear to a person viewing the drawings and are utilized only to facilitate describing the preferred embodiments.

DESCRIPTION

As shown in FIG. 1A, the present biopsy hand tool is indicated in general by the reference numeral 10. The biopsy hand tool 10 includes a handle 12.

As shown in FIG. 1B, the hand tool 10 further includes a stylus 14 having a distal end portion 16 and a proximal end portion 18 fixed to a stylus handle portion 20. The stylus 14 is preferably utilized for penetrating or drilling through relatively hard tissue such as bone cortex.

The stylus 14 is axially insertable into and withdrawable from and in close relationship with an elongate inner or capture tube 22. The inner tube 22 includes a distal end portion 24 and a proximal end portion 26 which is fixed to a capture tube handle portion 28. The inner tube 22 is axially insertable into and withdrawable from and in close relationship with an elongate outer tube 30. The outer tube 30 includes a distal end portion 32 and a proximal end portion 34 which is fixed to an outer tube handle portion 36. The inner tube 22 and outer tube 30 in combination may be referred to as a cannula. The inner tube 22 and outer tube 30 are preferably utilized to cut and take a sample of relatively soft tissue, with the outer tube 30 performing the initial cut in the axial direction and the inner tube 22 subsequently being rotated relative to the outer tube 30 to at least partially or completely cut the connection between the specimen and the in vivo tissue and capture the sample tissue in the cannula.

The handle 12 may include various arrangements for preventing or permitting rotation of the stylus 14, inner tube 22, and outer tube 30 and their handle portions 20, 28, and 36 relative to each other. These arrangements or means may include four tabs 38 mounted via pins on both sides of the outer tube handle portion 36 and pivotable therefrom to engage both sides of the inner tube handle portion 28. When engaged with inner tube handle portion 28, the tabs 38 prevent rotation of the inner tube 22 relative to the outer tube 30. When disengaged therefrom, the handle portion 28 may be turned to rotate the inner tube 22 relative to the outer tube 30. Such arrangements or means may further include a pair of integral extensions 40 projecting from the inner end of stylus handle portion 20 and engagable with holes 42 formed in the outer end of inner tube handle portion 28 for preventing rotation of the stylus 14 relative to the inner and outer tubes 22 and 30. For a linear advance or spiral rotation of the inner tube 22 relative to the outer tube 30, a spacer 43 is removed from between handle portions 28 and 36. Prior to its removal, it should be noted that spacer 43 may be held in position by tabs 38 which may be turned partially so as to disengage from handle portion 28 to permit rotation thereof, but still engage and contact spacer 43. It should be noted that spacer 43 may include a centrally positioned slot 43.1 extending laterally to one side for permitting the spacer 43 to be disengaged relative to the inner tube 22 and slid out from between the handle portions 28 and 36 without removal of the inner tube 22 from the outer tube 30.

As shown in FIGS. 2A–D, the distal end portion 16 of the stylus 14 is form fit and in close relationship to the inner surface of the distal end 24 of the inner tube 22. The stylus 14 includes a tip or pivot point 44 for initially biting into the bone cortex. The stylus 14 further includes a cutting edge 46 extending about the perimeter of the distal end portion 16. As shown in FIG. 2D, the stylus tip 44 is disposed off-center from an central axis 48 of the outer tube 30. The effective cutting length of the perimeter cutting edge 46 is the distance of a line 49 extending at a right angle relative to axis 48 of outer tube 30 from stylus tip 44 to a point 50 in line with a diametrically opposite side 52 of the stylus 22. The length of line 49 is greater than the radius of the distal end portion 32 of the outer tube 30. Accordingly, when the stylus 14 is rotated about its tip 44, its cutting edge 46 forms a hole 54 having a diameter greater than the diameter of the distal end portion 32 of the outer tube 30. Hence the outer tube distal end portion 32 is easily insertable into the bone cortex hole 54.

As shown in FIG. 2E, an alternate embodiment of the stylus 14 includes a stylus 56 whose surface 58 is cylindrical instead of being form fit with a tapering portion as shown in FIG. 2A.

As shown in FIGS. 3A–E, the distal end portion 32 of the outer tube 30 includes a cutting edge 60 forming an opening 62 into the inner tube 22. The cutting edge 60 extends about the perimeter of the opening 62 and obliquely relative to the axis of the outer tube 32. The cutting edge 60 is oval in shape since the cutting edge 62 is disposed at an angle to the axis of the outer tube 32. However, when viewed in the axial direction as shown in FIG. 3B, the cutting edge 60 takes a round form.

The distal end portion 32 of the outer tube 30 further includes a tapering portion 64 which tapers from the cutting edge 60 to a medial or cylindrical portion 66 of the outer tube 30 which in turn extends between the distal and proximal end portions 32 and 34. The distal end portion 32 includes first and second diametrically opposing sides 68, 70. The cutting edge 60 is tangential to the distal end portion 32 and cylindrical portion 66 at the first side 68. The opposing sides 68 and 70 he in a plane with the axis of the outer tube 30. A section 72 of the tapering portion 64 which intersects such plane has the greatest slope of the variably tapering portion 64 relative to the axis of the outer tube 30. The slope of the tapering portion 64 progressively decreases from both sides of such an intersection to the first opposing side 68 which has no slope relative to the axis, is tangential to the cutting edge 60, and is parallel to the axis of the outer tube 30. Such a structure permits the distal end portion 24 of the inner tube 22 (which includes slopes identical to the distal end portion 32 of outer tube 30) to rotate within the distal end portion 32 of the outer tube 30 and close off at least a portion of the opening 60 of the outer tube 30. It should be noted that a tip 73 of the cutting edge 60 lies on such intersection and in such plane.

Figure 10:
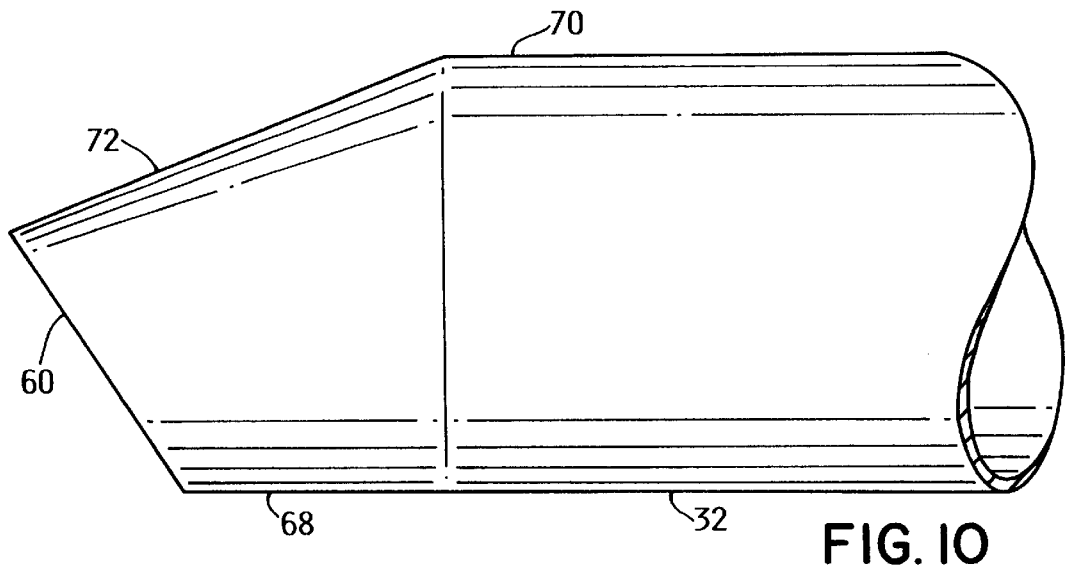
FIG. 10 shows an elevation view of the distal end portion of the outer tube of the present biopsy hand tool.
Figure 11:
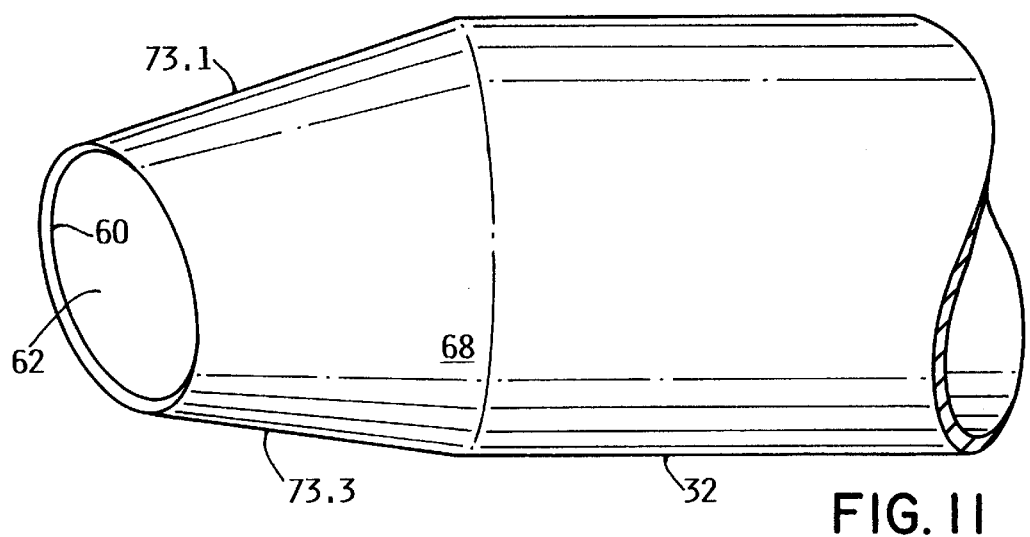
FIG. 11 shows an elevation view of the distal end portion of FIG. 10 rotated 90° along the longitudinal axis to show the varying slope of the distal end portion.
Figure 12:
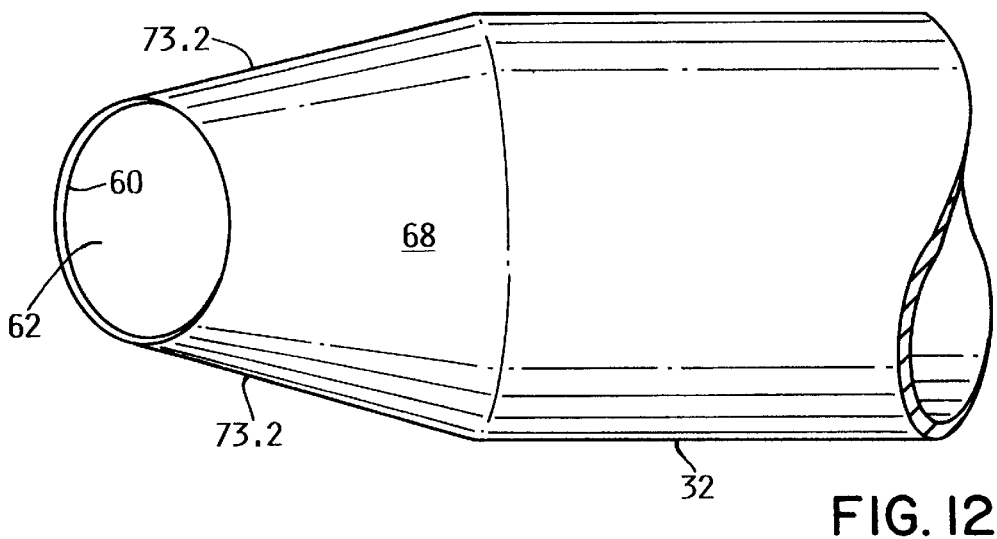
FIG. 12 shows an elevation view of the distal end portion of FIG. 10 rotated 180° along the longitudinal axis to show the varying slope of the distal end portion.

The varying slope of the distal end portion 32 is further shown in FIGS. 10, 11 and 12. FIG. 11 shows the distal end portion 32 rotated 90° from the view of FIG. 10 and FIG. 12 shows the distal end portion 32 rotated 90° from FIG. 11. Relative to the longitudinal axis of the outer tube 30, tapering portion 72 lies at the greatest slope, tapering portion 73.1 lies at a less great slope, tapering portions 73.2 lie at equal and lesser slopes than tapering portion 73.1, tapering portion 73.3 lies at a lesser slope than tapering portion 73.2, and side 68 lies at the least slope (no slope). Accordingly, tapering portion 64 is referred to as a variably tapering portion or as a progressively increasing or decreasing tapering portion. It should be noted that both the distal end portions 32 and 24 include such a variably tapering portions such that the distal end portion 24 may hide behind and rotate relative to the distal end portion 32. If the distal end portions 32 and 24 are formed by structures other than relatively thin walls, which is the preferred structure herein, such variably tapering portions are preferably given to the inner surface of the outer distal end portion 32 and the outer surface of the inner distal end portion 24 such that the inner distal end portion 24 may be hidden within and rotate relative to the outer distal end portion 32.

The distal end portion 24 of the inner tube 22 includes a concave distal edge 74 forming an opening 76. The distal edge 74 includes a cutting edge portion 78 (as shown in FIG. 3C) for cutting tissue and a beveled and slightly rounded or chamfered edge portion 80 for preventing tissue from catching thereon (as shown in FIGS. 3C and 3F). The chamfered edge portion 80 extends around about ten percent of the perimeter of the distal edge 74, with the cutting edge portion 78 extending around the remaining portion of the perimeter of the distal edge 74. The distal edge 74 as a whole curves progressively from a distal tip 82, where a tangent to the cutting edge portion 78 is at a relatively small angle or is parallel to the axis of the inner tube 22, to a first opposing side 84, where a tangent to the peak of the smooth edge portion 80 is at a light angle to the axis of the inner tube 22. If desired, edge 74 may have varying degrees of concavity or he in a plane.

It should be noted that the distal end portion 24 of the inner tube 22 includes a second opposing side 86 and a tapering portion 88 tapering from the distal edge 74 to a cylindrical portion 90 or the inner tube 22. Tapering portion 88 of the inner tube 22 is form fit to the tapering portion 64 of the outer tube 30 to permit ready rotation of the tapering portions 64 and 88 relative to each other.

It should further be noted that the outer tube opening 62 and the inner tube opening 76 are concentric with each other prior to rotation and become offset from each other when the inner tube 22 begins to rotate. Opening 62 is oval and opening 76 is somewhat egg-shaped, as shown in FIG. 3C. When viewed in the axial direction, each of the edges 60 and 74 of the openings 62 and 76 defines a circle.

The cutting edge 60 of the outer tube 30 lies in line with the inner surface of its distal end portion 32 and the cutting edge 78 of the inner tube 22 lies in line with the outer surface of its distal end portion 24 such that relative to each other the cutting edges 60 and 78 form a wedge to drive cut tissue apart and minimize the chances that tissue enters any space between the inner and outer tubes 22 and 30. This wedge like feature is most clearly illustrated in FIG. 3D where the tips 73 and 82 of the tubes 22 and 30 are shown.

The tapering portion 64 of the inner tube 22 lies adjacent to and generally aligned with the tapering portion 88 of the outer tube 30 prior to rotation of the tubes 22 and 30 relative to each other. Also in such position, the openings 62 and 76 and their edges 60 and 74 are aligned axially with each other. Further, the edges 60 and 74 are parallel when viewed from the axial direction. After rotation of the inner tube 22 relative to the outer tube 30 for 180°, the distal end portion 24 of the inner tube 22 at least partially closes off the outer tube opening 62 and the distal end portion 32 of the outer tube 30 at least partially closes off the inner tube opening 76. In such a position, the tapering portions 64 and 88 confront each other. Further, the cutting edges 60 and 78 when viewed in the axial direction appear to cross each other. Still further, while the inner and outer tubes 22 and 30 share an axis both prior to and after rotation, the center points or axes of the openings 62 and 76 become offset from each other when rotation is initiated.

It should be noted that the spacer 43 may be used with the embodiment shown in FIG. 3A. In such an embodiment, the spacer 43 is removed, and the inner tube 22 is advanced and rotated at the same time relative to outer tube 30 such that a spiral rotation is imparted to inner tube 22. As the inner tube cutting edge 78 extends obliquely to the axis of the inner tube 22, such a spiral advancement even further reduces the diameter of the connection between the specimen and the in vivo tissue. The final position of the inner tube tapering portion 88 with spiral advancement is indicated by the reference numeral 88.1 in FIG. 3A, while the final position of the inner tube tapering portion 88 with simple rotation of the inner tube 22 without removal of the spacer 43 is indicated by reference numeral 88.2 in FIG. 3A.

As shown in FIG. 4A–B, an alternate cannula 89 of the present invention includes a tapering portion 90 on an outer tube 91 which tapers for approximately one-half the diameter of the distal end portion 92. Accordingly, the outer tube opening 94 formed by cutting edge 96 has an effective diameter, when viewed in the axial direction, of about one-half the diameter of the outer tube 91. Likewise, an inner tube opening 98 formed by inner tube distal edge 99 (having cutting edge portions and rounded edge portions like distal edge 74) of an inner tube 100 has an effective diameter of approximately one-half of the inner tube 100. Hence, when the outer and inner tubes 91 and 100 are rotated relative each other, the connection between the specimen and the in vivo tissue is cut completely from its base tissue and the tissue sample is completely captured in the tubes 91 and 100. With the exception of the length of the taper, tapering portion 90 includes the varying slopes of tapering portion 64. Inner tube 100 includes a tapering portion 101 form fit to tapering portion 90. This alternate cannula embodiment may be referred to as a cannula which provides for 100% closure. It should be noted that tips 102, 103 of the tubes 91, 100 lie on or adjacent to the axis of the tubes 91, 100 and hence confront each other prior to, during, and after rotation of the tubes 91, 100 relative to each other. This type of cannula is preferably used to capture soft or semi-liquid samples.

As shown in FIG. 5, in one alternate embodiment of the invention, a cannula 104 includes an outer tube 106 with a curved distal end portion 108 with an opening 110 formed by a cutting edge 112. The cannula 104 further includes an inner tube 114 having a curved distal end portion 116 and a distal edge 118 (having cutting edge portions and rounded edge portions like distal edge 74). With such a cannula 104, the inner tube 114 may be formed of a resilient, perhaps thinner material such as a resilient sharpened metal, and initially pushed axially forwardly, after removal of spacer 43, and then rotated for a complete cutting of the connection between the specimen and the in vivo tissue and for 100% capture of the tissue sample. It should be noted that with cannula 104, complete capture of the tissue sample is possible without rotation of the outer and inner tubes 106 and 114 relative to each other. Such is accomplished by rotating the outer tube 106 for 360° when such is in the bone marrow so that the cutting edge 112 cuts to the same depth about the entirety of the connection between the specimen and the in vivo tissue, and then pushing the inner tube 114 axially forwardly relative to the outer tube. The inner side of curved portion 108 provides the resistance to deflect the distal edge 118 of inner tube 114 for 100% capture of tissue.

In yet another embodiment of the present invention, the outer tube 106 may include an anvil portion 119 opposite of the curved distal edge portion 108 and against which curved distal edge portion 116 may cut or shear the connection between the specimen and the in vivo tissue when spacer 43 is removed and handle portion 28 is moved forwardly relative to handle portion 36 such that inner tube 115 is moved forwardly relative to outer tube 106. In this embodiment also, complete capture of the tissue sample is possible without rotation of the outer and inner tubes 106 and 114 relative to each other. It should be noted that curved portion may if desired include the same varying slope as tapering portion 64. It should further be noted that a distal arc portion of cutting edge 118 participates in a shearing action with the anvil portion 119 which is integral with distal curved portion 108.

Figure 7:
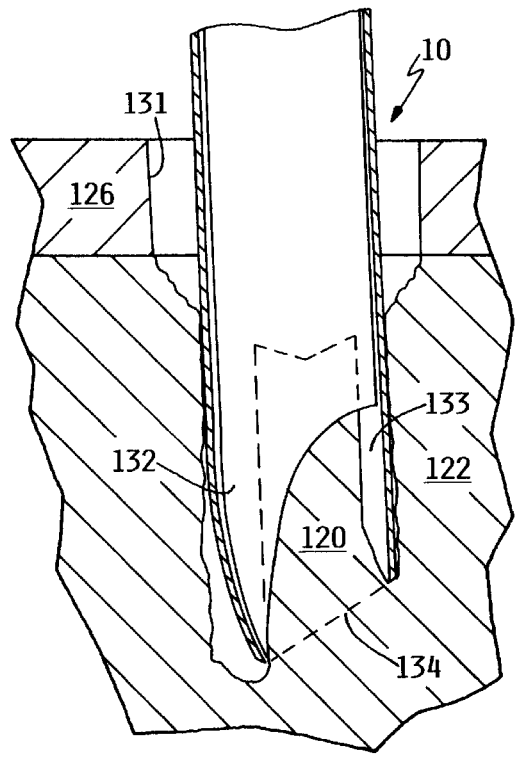
FIG. 7 shows a partially section view of the cannula of the present invention inserted through the opening formed by the stylus of FIG. 6, with the cannula having penetrated bone marrow (shown in section) to receive a tissue sample therein and having formed the connection between the specimen and the in vivo tissue.

In operation, as shown in FIGS. 6–9, the biopsy hand tool 10 is preferably utilized to take a tissue or core sample 120 of bone marrow 122 from a bone 124 having a bone cortex 126. As shown in FIG. 6, the stylus 14 forms a hole 128 in the bone cortex 126. Initially, the stylus 14 performs a needle-like function in that it penetrates the skin and tissue such as muscle tissue between the skin and the bone 124. Then the tip 94 makes contact and bites into with the bone cortex 126 and provides a pivot point for the subsequent carving or drilling like operation where the handle 12 is rotated, such as in a back and forth motion with the hand, and such that the cutting edge 46 carves the hole 128 in the bone cortex 126. Since the radius of the cutting edge 46 is greater than the diameter of the distal end portion 32 of the outer tube 30, the hole 128 is greater than the diameter of the distal end portion 32. As shown in FIG. 6, reference numeral 129 indicates a sidewall of an unfinished portion of the hole 128 and reference numeral 130 indicates a sidewall of a finished portion of hole 128. Sidewall 129 extends at a right angle to the surface of the bone. Sidewall 130 extends obliquely relative to the surface of the bone. In FIG. 7, reference numeral 131 indicates the sidewall of the finished hole 128. Sidewall 131 extends at a right angle to the surface of the bone.

After the stylus 14 has formed the hole 128, the stylus 14 is withdrawn from the inner and outer tubes 22 and 30 while such remain in the body and at least partially in the hole 128. Subsequently, prior to disengagement of the tabs 38 between the outer tube handle portion 36 and the inner tube handle portion 28, the outer and inner tubes 22 and 30 are inserted as a unit into the bone marrow 122 such that the cutting edge 60 cuts the specimen 120. During such an insertion into the bone marrow, the handle portions 36 and 38 are advanced as a unit, such as in a rotating back and forth hand motion. Since the effective diameter of the opening 62 is less than the diameter of the distal end portion 24 of the inner tube 22, the architecture of the sample 120 is preserved. Space between the inner tube 22 and the specimen 120 is indicated by reference numeral 132. Because the outer tube opening 62 is off-center from the axis of the outer tube 30 and generally tangential to the sidewall of the tube 30, space 132 is wider than a transverse space 133. After insertion of the outer tube 30 to the desired depth in the marrow 122, a connection 134 between the specimen and the in vivo tissue remains, connecting the specimen 120 to its underlying in vivo tissue 122.

Figure 8:
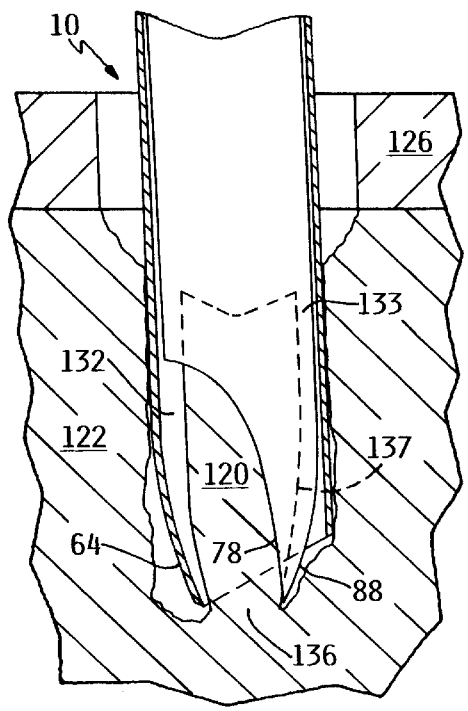
FIG. 8 shows the inner tube of the cannula of FIG. 7 after axial rotation of 180° relative the outer tube to at least partially cut the connection between the specimen and the in vivo tissue of FIG. 7.

As shown in FIG. 8, after the cannula has been inserted to the desired depth in the bone marrow 122, the handle portions 36 and 28 are disengaged relative each other, such as by the tabs 38, and the inner tube 22 is rotated relative to the outer tube 30. As the inner tube 22 is rotated, its cutting edge 78 at least partially cuts, or completely cuts, the tissue connection 134 depending on the degree of "capture" for the biopsy device used. A tissue connection 136 of a reduced size is shown in FIG. 8 after the inner tube 22 has been rotated for 180° relative to the outer tube 30. FIG. 8 also shows a taper 137 provided to the specimen 120 by the cutting edge 78 of the distal end portion 24 of the inner tube 22. FIG. 8 further shows the inner tube tapering portion 88 confronting the outer tube tapering portion 64 so as to capture or hold the specimen 120 in the inner tube 30. Further, since most of the cylinder like specimen 120 has generally the diameter of the outer tube cutting edge 62, the chances are minimal that the larger specimen 120 can slip out the opening that remains between the inner and outer tubes 22 and 30. Such an opening is indicated by the reference numeral 138 in FIG. 3B. As shown in FIG. 3B, the opening 138 takes a lenticular shape, the area of which is less than area of the outer tube opening 62 and diameter or average diameter of the specimen 120 and separates the tissue sample from the in vivo tissue. Lenticular opening 138 is sufficiently small to obstruct the specimen 120 from slipping out or being pulled back out of the cannula.

Figure 9:
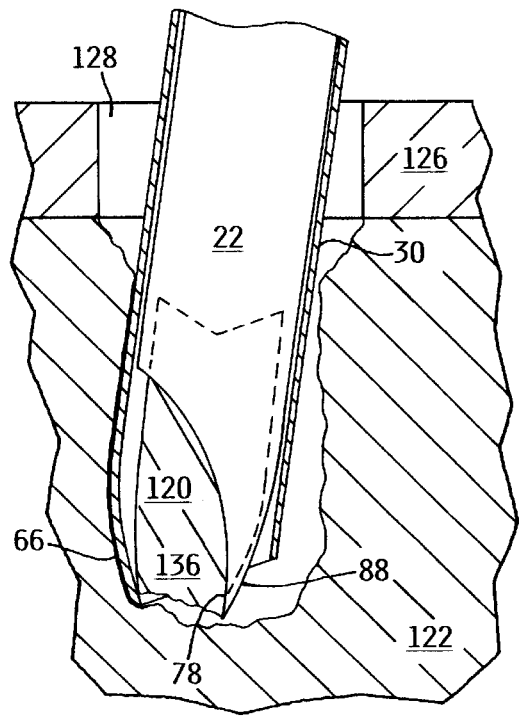
FIG. 9 shows the cannula tilted relative to the hole formed by the stylus and illustrates the outer tube of the cannula of FIG. 8 cutting off the connection between the specimen and the in vivo tissue by capturing the specimen.

As shown in FIG. 9, after 180° rotation of the inner tube 22 relative to the outer tube 30, the inner and outer tubes 22 and 30 may as a unit be tilted in the hole 128 relative to the bone cortex 126 as the hole 128 has a greater diameter than the outer tube 30. Such tilting permits one of the tube cutting edges, preferably the inner tube cutting edge 78, to cut off the tissue connection 136 to sever the specimen 120 from the underlying in vivo bone marrow 122. Then, with the specimen 120 captured in the inner tube 22 and with the tapering portions 64 and 88 confronting each other, the inner and outer tubes 22 and 30 are withdrawn from the bone 124 and body. Subsequently, to remove the specimen 120 from the cannula, the inner tube 22 is axially withdrawn completely from the outer tube 30 whereupon the specimen 120 may be gently removed from the biopsy hand tool 10 such as by a tapping of the inner tube 22 against the palm of the hand or other surface, whereupon the specimen 120 will slide out.

Figure 13:
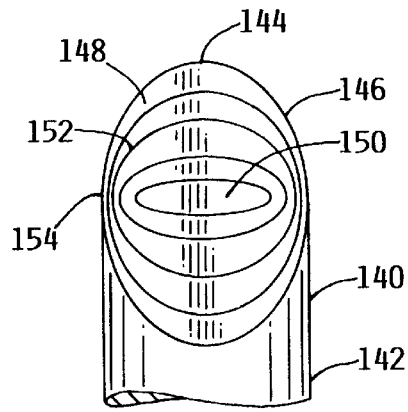
FIG. 13 shows a diagrammatic view of one scoop-like embodiment of the distal end portion of the stylus, with contour lines showing the relative depths of the scoop.

FIG. 13 shows a distal end portion 140 of a stylus 142 of the present invention. The distal end portion 140 includes a distal tip 144 for initially biting into bone cortex. The distal end portion 140 further includes an elliptical cutting edge 146. Within the cutting edge 146 is formed a scoop 148. The scoop 148 includes at its greatest depth relative a medial or central region 150. As indicated by a plurality of elevational lines 152, the slope of the surface of the scoop 148 is relatively gradual from the distal tip 144 to the central region 150 while the slope of the surface of the scoop 148 is relatively steep from a lateral side portion 154 to the central region 150. The distal tip 144 if formed on a longitudinal portion of the cutting edge 146.

Figure 14:
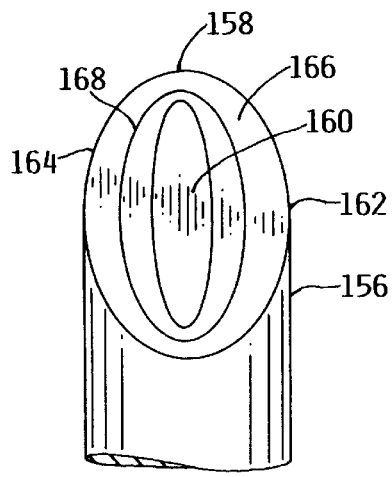
FIG. 14 shows a diagrammatic view of another scoop-like embodiment of the distal end portion of the stylus, with contour lines showing the relative depths of the scoop.
Figure 15:
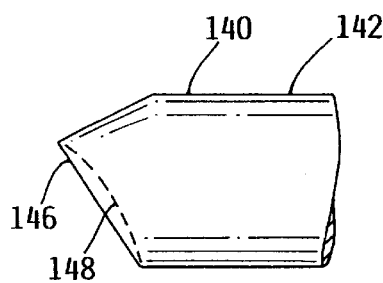
FIG. 15 shows a side view of the scoop-like embodiment of FIG. 13.

FIG. 14 shows another embodiment of the stylus having a scoop-like distal end portion. This scoop-like distal end portion 156 includes a tip 158, a central region 160, and a lateral portion 162 of a cutting edge 164. The slope of the surface of the scoop 166 is relatively steep from the tip 158 to the central region 160 and relatively gradual from the lateral portion 162 to the central region 160. These slopes are indicated by the elevational lines 168.

It should be noted that the scoop 148 shown in FIG. 13 is most preferred and that such stylus is preferably used with the outer tube 30 and inner tube 22.

It should be noted that for the purposes of the present invention, the term "diameter" may refer to shapes other than circles and cylinders. Such other shapes include oval shapes, ellipsoids, squares, rectangles, hexagons, etc. The term "diameter" herein may mean size, width, height, or thickness.

The size of the diameter of the inner tube 22 may be that which is effective to take a biopsy sample. For example, the inner tube 22, and its outer tube 30, may have a sufficiently small diameter to take a fine needle biopsy. Typically, the gauge of the inner tube 22 is between about 8 and about 22 gauge or of a gauge sufficiently small to take the fine needle biopsy.

Thus since the invention disclosed herein may be embodied in other specific forms without departing from the spirit or general characteristics thereof some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

I claim:

1. A hand tool for taking a sample of body tissue, comprising, in combination:
   a) a handle;
   b) an outer elongate tube having proximal and distal end portions, with the proximal end portion of the tube being fixed to a portion of the handle, with the distal end portion of the tube having a cutting edge for cutting tissue, with the cutting edge forming a distal opening through which the sample of body tissue is received, with the outer tube having a tubular sample-receiving portion integral therewith for receiving the sample of body tissue, with the tubular sample-receiving portion extending at least partially from the cutting edge toward the proximal end portion of the outer tube, with the sample-receiving portion having an axis and an outside diameter; and
   c) a stylus in the outer elongate tube for carving a hole in tissue through which the outer elongate tube is insertable for taking the sample of body tissue, with the stylus being axially removable at least from the distal end portion of the tube to permit the outer elongate tube to take the sample of body tissue, with the stylus having proximal and distal end portions, with the proximal end portion of the stylus being fixed to a portion of the handle, with the distal end portion of the stylus having a cutting edge for cutting tissue to form the hole and further having a diameter less than the diameter of the outer tube, with the cutting edge of the stylus having a tip for biting into tissue and about which the stylus is pivotable, with the tip extending beyond the distal end portion of the outer tube, with the cutting edge of the stylus having an effective cutting radius more than one-half the outside diameter of the tubular sample-receiving portion such that the hole carved in the tissue by rotation of the stylus about the tip has a diameter greater than the outside diameter of the tubular sample-receiving portion and such that the tubular sample-receiving portion of the outer tube is extendible relatively freely into and tiltable relative to the opening formed by the stylus.

2. The hand tool of claim 1 wherein the tip is off-center from the axis of the tubular sample-receiving portion of the outer tube.

3. The hand tool of claim 1 wherein the stylus is slideable in the axial direction out of the outer tube such that the distal end portion of the stylus slides from the distal end portion of the outer tube to and out of the proximal end portion of the outer tube.

4. The hand tool of claim 1 wherein the proximal end portion of the outer tube and the proximal end portion of the stylus are fixed to different portions of the handle, with the different portions of the handle being readily disconnectable from each other.

5. The hand tool of claim 1 wherein the cutting edge of the outer elongate tube is disposed at an angle relative to the axis of the tubular sample-receiving portion whereby the cutting edge of the outer elongate tube slices easily into tissue.

6. The hand tool of claim 5 wherein the cutting edge of the outer elongate tube includes a tip and wherein the cutting edge of the stylus includes a less distal portion, wherein the tip of the outer elongate tube lies at a greater axial distance from the handle than the less distal portion of the cutting edge of the stylus such that the distal end of the stylus is in close relationship with the distal end of the outer tube.

7. A hand tool for taking a sample of body tissue, comprising, in combination:
   a) a handle;
   b) an outer elongate tube having proximal and distal end portions, with the proximal end portion of the outer elongate tube being fixed to a portion of the handle and with the distal end portion of the outer elongate tube having a cutting edge and an opening formed by said cutting edge such that when the distal end portion of the outer elongate tube is manipulated into the body tissue, the sample of body tissue is at least partially cut by the cutting edge of the outer elongate tube and received into the hand tool;
   c) an inner elongate tube inside of and in close relationship with the outer elongate tube, with the inner elongate tube having proximal and distal end portions, with the proximal end portion of the inner elongate tube being fixed to a portion of the handle and with the distal end portion of the inner tube being adjacent to the distal end portion of the outer tube and having an opening interacting with the opening of the outer elongate tube and through which the sample is received when cut by the cutting edge of the outer elongate tube, with the opening of the inner elongate tube being formed by a distal edge, with at least a portion of the distal edge being a cutting edge such that movement of the inner elongate tube relative to the outer elongate tube permits the cutting edge of the inner elongate tube to further cut the body tissue sample to increase the chances that the body tissue sample is separated from the body for withdrawal therefrom in the tool, and with the opening of the inner elongate tube being at least partially closed by the distal end portion of the outer elongate tube after such movement to capture the sample of body tissue; and
   d) wherein the distal end portion of the inner elongate tube includes a sample-receiving portion having a first diameter when viewed in the axial direction and wherein the cutting edge of the outer elongate tube has a second diameter when viewed in the axial direction, with the second diameter being less than the first diameter such that the diameter of the body tissue sample cut by the first cutting edge is less than the diameter of the sample receiving portion of the inner tube when the tool is manipulated in the axial direction whereby the architecture of the body tissue sample remains unaltered.

8. The hand tool of claim 7 wherein the outer elongate tube has an axis and wherein each of the distal end portions of the tubes includes a tapering portion tapering at an oblique angle relative to the axis and tapering toward the respective cutting edges, with the tapering portion of the inner elongate tube initially being in an adjacent relationship with the tapering portion of the outer elongate tube and further being rotatable away from such adjacent relationship when the inner elongate tube is rotated relative to the outer elongate tube such that the tapering portion of the inner elongate tube is disposable transversely of the tapering portion of the outer elongate tube to confront opposing sides of the body tissue sample to capture the body tissue in the hand tool.

9. The hand tool of claim 7 wherein the outer elongate tube has an axis and wherein the cutting edge of the outer elongate tube is disposed obliquely relative to the axis, with the distal end portion and cutting edge of the inner elongate tube initially being disposed inwardly of the opening of the outer elongate tube, with at least a portion of the distal end portion of the inner elongate tube closing off the opening of the outer elongate tube when the inner elongate tube is rotated relative to the outer elongate tube to better capture the body tissue sample in the hand tool.

10. A hand tool for taking a sample of body tissue, comprising, in combination:
  a) a handle;
  b) an outer elongate tube having proximal and distal end portions, with the proximal end portion of the outer elongate tube being fixed to a portion of the handle and with the distal end portion of the outer elongate tube having a cutting edge and an opening formed by said cutting edge such that when the distal end portion of the outer elongate tube is manipulated into the body tissue, the sample of body tissue is at least partially cut by the cutting edge of the outer elongate tube and received into the hand tool;
  c) an inner elongate tube inside of and in close relationship with the outer elongate tube, with the inner elongate tube having proximal and distal end portions, with the proximal end portion of the inner elongate tube being fixed to a portion of the handle and with the distal end portion of the inner tube being adjacent to the distal end portion of the outer tube and having an opening interacting with the opening of the outer elongate tube and through which the sample is received when cut by the cutting edge of the outer elongate tube, with the opening of the inner elongate tube being formed by a distal edge, with at least a portion of the distal edge being a cutting edge such that movement of the inner elongate tube relative to the outer elongate tube permits the cutting edge of the inner elongate tube to further cut the body tissue sample to increase the chances that the body tissue sample is separated from the body for withdrawal therefrom in the tool, and with the opening of the inner elongate tube being at least partially closed by the distal end portion of the outer elongate tube after such movement to capture the sample of body tissue; and
  d) wherein each distal end portion of the outer and inner elongate tubes has an axis and first and second opposing sides, with the opening of each distal end portion being of a smaller diameter than its respective tube, with the edge forming each opening being tangential to the first opposing side of its respective tube, and with the axis and first and second opposing sides being in a plane; and with each distal end portion including a tapering portion extending from its respective opening to a cylindrical portion of its respective distal end portion, with the cylindrical portion being tangential to its respective first opposing side, with each tapering portion having a slope relative to the axis, with the slope being greatest where the tapering portion intersects the plane, with the slope progressively decreasing from such an intersection to the first opposing side of each tube which is tangential to its respective cylindrical portion, whereby the distal end portion of the inner elongate tube is readily rotatable within the distal end portion of the outer elongate tube.

11. The hand tool of claim 7 wherein the tubes are rotatable relative to each other and wherein:
  a) prior to rotation of the tubes relative to each other, the openings of the tubes are generally aligned with each other and the distal end portions of the tubes are generally aligned with each other; and
  b) after rotation of the tubes relative to each for 180°, the openings of the tubes are offset from each other and the distal end portion of the tubes are offset from each other, with the distal end portion of each of the tubes at least partially closing off the opening of the other tube.

12. The hand tool of claim 11 wherein, after rotation of the tubes relative to each other for 180°, the distal end portions of each of the tubes completely close off the opening of the other tube whereby soft or semi-liquid body tissue samples may be captured.

13. The hand tool of claim 12 wherein the diameter of the opening in the outer elongate tube is about one-half the diameter of a portion of the outer elongate tube containing the sample of body tissue.

14. The hand tool of claim 7 wherein each of the distal end portions includes a distal extremity, with each of the distal extremities after rotation of the tubes confronting each other prior to, during, and after rotation of the distal end portions relative to each other.

15. A hand tool for taking a sample of body tissue, comprising, in combination:
  a) a handle;
  b) an outer elongate tube having proximal and distal end portions, with the proximal end portion of the outer elongate tube being fixed to a portion of the handle and with the distal end portion of the outer elongate tube having a cutting edge and an opening formed by said cutting edge such that when the distal end portion of the outer elongate tube is manipulated into the body tissue, the sample of body tissue is at least partially cut by the cutting edge of the outer elongate tube and received into the hand tool;
  c) an inner elongate tube inside of and in close relationship with the outer elongate tube, with the inner elongate tube having proximal and distal end portions, with the proximal end portion of the inner elongate tube being fixed to a portion of the handle and with the distal end portion of the inner tube being adjacent to the distal end portion of the outer tube and having an opening interacting with the opening of the outer elongate tube and through which the sample is received when cut by the cutting edge of the outer elongate tube, with the opening of the inner elongate tube being formed by a distal edge, with at least a portion of the distal edge being a cutting edge such that movement of the inner elongate tube relative to the outer elongate tube permits the cutting edge of the inner elongate tube to further cut the body tissue sample to increase the chances that the body tissue sample is separated from the body for withdrawal therefrom in the tool, and with the opening of the inner elongate tube being at least partially closed by the distal end portion of the outer elongate tube after such movement to capture the sample of body tissue; and d) wherein the inner elongate tube includes an axis, and wherein the distal edge of the inner elongate tube includes a greater distal edge section located at a greater axial distance from the handle and a lesser distal edge section located at a lesser axial distance from the handle, with the distal edge curving from the greater distal section to the lesser distal section.

16. The hand tool of claim 15 wherein the distal edge of the inner tube curves progressively from the greater distal edge section to the lesser distal edge section.

17. The hand tool of claim 16 wherein tangents to the distal edge in the greater distal edge section lie at a lesser angle relative to the axis than tangents to the distal edge in the lesser distal edge section.

18. The hand tool of claim 15 wherein the distal edge of the lesser distal section includes a noncutting portion having a radius.

19. A hand tool for taking a sample of body tissue, comprising, in combination:

a) a handle;

b) an outer elongate tube having proximal and distal end portions, with the proximal end portion of the outer elongate tube being fixed to a portion of the handle and with the distal end portion of the outer elongate tube having a cutting edge and an opening formed by said cutting edge such that when the distal end portion of the outer elongate tube is manipulated into the body tissue, the sample of body tissue is at least partially cut by the cutting edge of the outer elongate tube and received into the hand tool;

c) an inner elongate tube inside of and in close relationship with the outer elongate tube, with the inner elongate tube having proximal and distal end portions, with the proximal end portion of the inner elongate tube being fixed to a portion of the handle and with the distal end portion of the inner tube being adjacent to the distal end portion of the outer tube and having an opening interacting with the opening of the outer elongate tube and through which the sample is received when cut by the cutting edge of the outer elongate tube, with the opening of the inner elongate tube being formed by a distal edge, with at least a portion of the distal edge being a cutting edge such that movement of the inner elongate tube relative to the outer elongate tube permits the cutting edge of the inner elongate tube to further cut the body tissue sample to increase the chances that the body tissue sample is separated from the body for withdrawal therefrom in the tool, and with the opening of the inner elongate tube being at least partially closed by the distal end portion of the outer elongate tube after such movement to capture the sample of body tissue; and d) wherein the outer elongate tube includes an inner surface and wherein the inner elongate tube includes an outer surface in close relationship with the inner surface of the outer tube, with the cutting edge of the outer elongate tube including a cutting tip substantially in line with its inner surface, with the cutting edge of the inner elongate tube including a cutting tip substantially in line with its outer surface such that the cutting edges form substantially the shape of a wedge to wedge body tissue apart.

20. A hand tool for taking a sample of body tissue, comprising, in combination:

a) a handle;

b) an outer elongate tube having proximal and distal end portions, with the proximal end portion of the outer elongate tube being fixed to a portion of the handle and with the distal end portion of the outer elongate tube having a cutting edge and an opening formed by said cutting edge such that when the distal end portion of the outer elongate tube is manipulated into the body tissue, the sample of body tissue is at least partially cut by the cutting edge of the outer elongate tube and received into the hand tool;

c) an inner elongate tube inside of and in close relationship with the outer elongate tube, with the inner elongate tube having proximal and distal end portions, with the proximal end portion of the inner elongate tube being fixed to a portion of the handle and with the distal end portion of the inner tube being adjacent to the distal end portion of the outer tube and having an opening interacting with the opening of the outer elongate tube and through which the sample is received when cut by the cutting edge of the outer elongate tube, with the opening of the inner elongate tube being formed by a distal edge, with at least a portion of the distal edge being a cutting edge such that movement of the inner elongate tube relative to the outer elongate tube permits the cutting edge of the inner elongate tube to further cut the body tissue sample to increase the chances that the body tissue sample is separated from the body for withdrawal therefrom in the tool, and with the opening of the inner elongate tube being at least partially closed by the distal end portion of the outer elongate tube after such movement to capture the sample of body tissue; and d) wherein the cutting edge of the outer elongate tube, when viewed in the axial direction, forms a first shape having a first periphery, and wherein the cutting edge of the inner elongate tube, after relative rotation of the tubes for 180°, extends across the periphery when viewed in the axial direction so as to separate the first shape into at least two parts.

21. The hand tool of claim 7 wherein the proximal end of the outer tube and the proximal end of the inner tube are fixed to different portions of the handle, with the different portions of the handle being rotatable relative to each other for a rotation of the tubes relative to each other.

22. A hand tool for taking a sample of body tissue, comprising, in combination:

a) a handle;

b) an outer elongate tube having proximal and distal end portions, with the proximal end portion of the outer elongate tube being fixed to a portion of the handle and with the distal end portion of the outer elongate tube having a cutting edge and an opening formed by said cutting edge such that when the distal end portion of the outer elongate tube is manipulated into the body tissue, the sample of body tissue is at least partially cut by the cutting edge of the outer elongate tube and received into the hand tool;

c) an inner elongate tube inside of and in close relationship with the outer elongate tube, with the inner elongate tube having proximal and distal end portions, with the proximal end portion of the inner elongate tube being fixed to a portion of the handle and with the distal end portion of the inner tube being adjacent to the distal end portion of the outer tube and having an opening interacting with the opening of the outer elongate tube and through which the sample is received when cut by the cutting edge of the outer elongate tube, with the opening of the inner elongate tube being formed by a distal edge, with at least a portion of the distal edge being a cutting edge such that movement of the inner elongate tube relative to the outer elongate tube permits the cutting edge of the inner elongate tube to further cut the body tissue sample to increase the chances that the body tissue sample is separated from the body for withdrawal therefrom in the tool, and with the opening of the inner elongate tube being at least partially closed by the distal end portion of the outer elongate tube after such movement to capture the sample of body tissue;

d) with the inner tube being advanceable from a first fixed position forwardly relative to the outer tube to a second fixed position; and e) with the distal end portion of the outer tube having a curved portion having a slope oblique to the axis of the outer tube; and the distal end portion of the inner tube being resilient and engagable with the curved portion such that the distal end portion of the inner tube is directed obliquely to the axis of the outer tube when the inner tube is advanced to the second fixed position.

23. The hand tool of claim 22 wherein the distal end portion of the outer tube includes an anvil portion engagable by the distal end portion of the inner tube.

24. A hand tool for taking a sample of body tissue, comprising, in combination:

a) a handle;

b) an outer elongate tube with proximal and distal end portions, with the proximal distal end portion being fixed to a portion of the handle, with the distal end portion of the outer tube comprising a cutting edge for cutting the sample of body tissue, with the cutting edge forming an opening in the distal end portion of the outer tube through which the sample is received;

c) an inner elongate tube inside of the outer elongate tube and in close relationship therewith, with the inner elongate tube having proximal and distal end portions, with the proximal end portion of the inner elongate tube being fixed to a portion of the handle, with the distal end portion of the inner elongate tube being adjacent to and disposable inside of the distal end portion of the outer elongate tube, with the distal end portion of the inner elongate tube comprising an opening with a distal edge, with at least a portion of the distal edge forming a cutting edge, with the distal end portion of the inner elongate tube further comprising a sample-receiving portion of a greater diameter than the opening of the outer elongate tube for receiving the body tissue sample such that the architecture of the body tissue sample remains unaltered, with the openings interacting with each other prior to relative movement of the tubes and with each of the distal end portions of the tubes at least partially closing off the opening of the other tube after at least partial movement of the tubes relative to each other to at least partially capture the body tissue sample in the hand tool; and d) a stylus in the inner elongate tube and having proximal and distal end portions, with the proximal end portion of the stylus fixed to a portion of the handle, with the distal end portion of the stylus being disposed beyond the opening of the outer elongate tube for penetrating body tissue prior to the outer and inner elongate tubes cutting and capturing the body tissue sample.

25. The hand tool of claim 24 wherein the sample-receiving portion of the outer elongate tube includes an outer surface having a diameter and wherein the distal end portion of the stylus includes a cutting edge, with the cutting edge having a tip about with the stylus rotates such that effective cutting length of the cutting edge is greater than one-half the length of the diameter of the outer surface of the sample-receiving portion of the outer elongate tube and such that the cutting edge of the stylus forms an opening in body tissue of a grater diameter than the outer surface of the sample-receiving portion of the outer elongate tube whereby the distal end portion of the hand tool may be readily inserted in the opening in the body tissue formed by the stylus.

26. The hand tool of claim 25 wherein the proximal ends of the outer elongate tube, the inner elongate tube, and the stylus are fixed to different portions of the handle, with the portions being readily disconnectable from each other.

27. The hand tool of claim 24 wherein the tubes are rotatable relative to each other to cut and capture the sample.

28. A method for taking a sample of body tissue with a cannula, with the cannula having a first and second distal end portions movable relative to each other with respective cutting edges, with the first distal end portion being a tube portion having an opening defined by the first cutting edge, with the method comprising, in combination, the steps of:

a) inserting the cannula in the axial direction into the tissue such that the cutting edge of the tube portion makes a cut in the body tissue in the axial direction, with body tissue cut by the tube portion being received into the opening and into the cannula, with the body tissue in the cannula remaining connected through the opening to body tissue outside of the cannula;

b) moving the distal end portions relative to each other such that the cutting edge of the second distal end portion makes a cut in the body tissue at an angle relative to the axial direction such that the body tissue in the cannula is at least partially cut from the body tissue outside of the cannula and such that at least one of the distal end portions at least partially closes off the opening to capture the sample; and c) wherein the step of moving the distal end portions relative to each other comprises the step of sliding the distal end portions relative to each other in generally a longitudinal direction and at an angle to the axial direction to make the cut in the body tissue at an angle relative to the axial direction.

29. A hand tool for taking a sample of body tissue, comprising, in combination:

a) a handle;

b) a stylus for forming a hole in the tissue prior to the sample being taken by the tool, with the stylus having proximal and distal end portions, with the proximal end portion engaged to a portion of the handle, with the distal end portion of the stylus comprising, in combination: a cutting edge with a lateral portion, a distal tip on a longitudinal portion of the cutting edge, and a scoop formed radially inwardly of the cutting edge; and c) wherein the scoop comprises a central region and a surface, with the surface of the scoop from the lateral portion of the cutting edge to the central region having a greater slope than the surface of the scoop from the tip to the central region.

30. The hand tool of claim 29 and further comprising a cannula interacting with the stylus for taking the sample of body tissue.

* * * * *